United States Patent
Jürgens et al.

(10) Patent No.: US 9,993,286 B2
(45) Date of Patent: Jun. 12, 2018

(54) HIGH-FREQUENCY SURGICAL DEVICE

(71) Applicant: OLYMPUS WINTER & IBE GMBH, Hamburg (DE)

(72) Inventors: Thorsten Jürgens, Hamburg (DE); Dennis Trebbels, Bad Schwartau (DE); Thomas Freitag, Hamburg (DE); Josef Bartolic, Karlsruhe (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 443 days.

(21) Appl. No.: 14/423,337

(22) PCT Filed: Jul. 17, 2013

(86) PCT No.: PCT/EP2013/002118
§ 371 (c)(1),
(2) Date: Feb. 23, 2015

(87) PCT Pub. No.: WO2014/029455
PCT Pub. Date: Feb. 27, 2014

(65) Prior Publication Data
US 2015/0201992 A1 Jul. 23, 2015

(30) Foreign Application Priority Data
Aug. 22, 2012 (DE) .................. 10 2012 016 563

(51) Int. Cl.
*A61B 18/18* (2006.01)
*A61B 18/14* (2006.01)
(Continued)

(52) U.S. Cl.
CPC .......... *A61B 18/14* (2013.01); *A61B 18/1206* (2013.01); *A61B 2018/0016* (2013.01);
(Continued)

(58) Field of Classification Search
CPC .. A61B 2018/00577; A61B 2018/0016; A61B 18/1206
(Continued)

(56) References Cited

U.S. PATENT DOCUMENTS 5,462,545 A 10/1995 Wang et al.
6,149,620 A * 11/2000 Baker .................... A61B 18/12
604/22

(Continued)

FOREIGN PATENT DOCUMENTS

CN 1781462 A 6/2006
CN 102164556 A 8/2011
(Continued)

OTHER PUBLICATIONS

Feb. 24, 2015 International Preliminary Report on Patentability issued in Application No. PCT/EP2013/002118.
Oct. 24, 2013 International Search Report issued in Application No. PCT/EP2013/002118.

*Primary Examiner* — Amanda Patton
*Assistant Examiner* — Philip C Edwards
(74) *Attorney, Agent, or Firm* — Oliff PLC

(57) ABSTRACT

A high-frequency surgical device for treating a tissue surface, device having an electrode device, in which a first electrode is formed on a working surface intended for contact with the tissue, and having a high-frequency generator, to the one pole of which the first electrode can be connected for operation. The surgical device is wherein a second electrode is formed on the working surface which electrode can be connected to the same pole, wherein a control device is connected to this and is designed initially to connect the first electrode and then to switch on the second electrode.

10 Claims, 2 Drawing Sheets

(51) Int. Cl.
*A61B 18/12* (2006.01)
*A61B 18/00* (2006.01)
*A61B 90/00* (2016.01)

(52) U.S. Cl.
CPC ............... *A61B 2018/00577* (2013.01); *A61B 2018/00583* (2013.01); *A61B 2018/00648* (2013.01); *A61B 2018/00654* (2013.01); *A61B 2018/00708* (2013.01); *A61B 2018/00875* (2013.01); *A61B 2018/00892* (2013.01); *A61B 2018/00958* (2013.01); *A61B 2018/122* (2013.01); *A61B 2018/124* (2013.01); *A61B 2018/1417* (2013.01); *A61B 2018/1467* (2013.01); *A61B 2018/1472* (2013.01); *A61B 2090/065* (2016.02)

(58) Field of Classification Search
USPC ........................................................... 606/41
See application file for complete search history.

(56) References Cited

U.S. PATENT DOCUMENTS

| | | |
|---|---|---|
| 2005/0149012 A1 | 7/2005 | Penny et al. |
| 2008/0300590 A1 | 12/2008 | Home et al. |
| 2009/0125021 A1 | 5/2009 | Brommersma |
| 2010/0010485 A1 | 1/2010 | West, Jr. |

FOREIGN PATENT DOCUMENTS

| | | |
|---|---|---|
| DE | 102007054438 A1 | 5/2009 |
| EP | 1637087 A2 | 3/2006 |
| EP | 1658817 A1 | 5/2006 |
| JP | 2011-527612 A | 11/2011 |
| WO | 0054683 A1 | 9/2000 |

* cited by examiner

HIGH-FREQUENCY SURGICAL DEVICE

The invention relates to a high-frequency surgical device according to the preamble of claim 1.

Such a device is known from DE 10 2007 054 438 A1. Using the electrode, this and other known generic designs are brought into surface contact with a tissue surface. When the high-frequency current is switched on, the tissue surface is heated greatly. Depending on the intended application, this may be used for cauterizing, i.e., for sealing bleeding surfaces, or for vaporization, i.e., for evaporation and thus ablation of tissue volume.

Important fields of application, although these are not the only ones, include urology and gynecology, where the work is performed in fluid. Monopolar arrangements use a poorly conducting fluid and current flow from the tissue contact through the body up to a neutral electrode arranged on the outside of the body. More recent methods work with a highly conductive fluid and with a neutral electrode which is in contact with the fluid and generates the essential current flow through the fluid.

Vaporization has recently often been performed in a highly conductive fluid, e.g., in saline (NaCl solution). Using a plasma layer that forms on the electrode, the tissue surface is heated to an extreme extent and vaporized. Large volumes of tissue can thus be ablated very easily, e.g., when treating the prostate.

Work on tissue surfaces in two dimensions can be performed particularly well using the electrode. With the known design, the large electrode surface area, which permits a high operating efficiency, is advantageous. However, the poor ignition performance is a disadvantage.

The ignition performance depends on the current density on the electrode surface. The current density depends on the size of the electrode surface. An advantageously large electrode surface leads to a low current density and to poor ignition. In many cases, ignition comes about only with uncertainty and a delay. The plasma collapses with even a slight worsening of the tissue contact and must be ignited again. The operator must therefore proceed with a very fine touch.

In addition, there is a heat problem. If the device must be ignited frequently, the temperature of the tissue may rise in an unwanted manner.

The object of the present invention is to improve upon the handling and the heat problem in the case of a generic device.

This object is achieved with the features of the characterizing part of claim 1.

According to the invention, multiple electrodes are operated, namely, first, a first electrode and then a second electrode or several more electrodes in addition. All the electrodes are connected to the same terminal of the high-frequency generator. This means that the electrodes operate first with only a part of the area and then additional parts of the area are added. However, this means that, at first, only a small electrode area is functional. This promotes a very high current density, i.e., reliable ignition. Once the plasma is burning, the second electrode can be switched on and will ignite immediately. Thus, with this invention, the advantages of the good ignition performance of a small electrode can be combined with the advantages of the high operating efficiency of a large electrode.

The advantageous features of claim 2 ensure that the control unit automatically triggers the electrode to be switched on. The operator need not be concerned about it. The operator always has reliable ignition performance.

According to claim 3, switching on the electrode is advantageously made a function of tissue contact. This can be combined with other measures and in turn yields an improved convenience in operation for the operator.

The tissue contact with the features of claim 4 can be detected automatically. Two electrodes that are present anyway are advantageously used for this detection, with an impedance measurement being performed between them.

According to claim 5, the electrode may advantageously be switched on by band and/or with a conventional foot switch.

The features of claim 6 are advantageously provided. The subdivision of the second electrode into a plurality of parts may permit advantages in the arrangement of the electrode on a working surface of any desired shape.

Claim 7 protects the electrode unit with the control unit of the device according to the invention.

Claim 8 protects the high-frequency generator with the control unit of the device according to the invention.

The drawing illustrates the invention schematically as an example, in which:

FIG. 1 shows a device 1 for high-frequency surgical treatment of a tissue surface, which is not shown in the drawings. In a common application case, a hypertrophic prostate is to be ablated by vaporization in a conductive fluid, for example.

Figure 1:
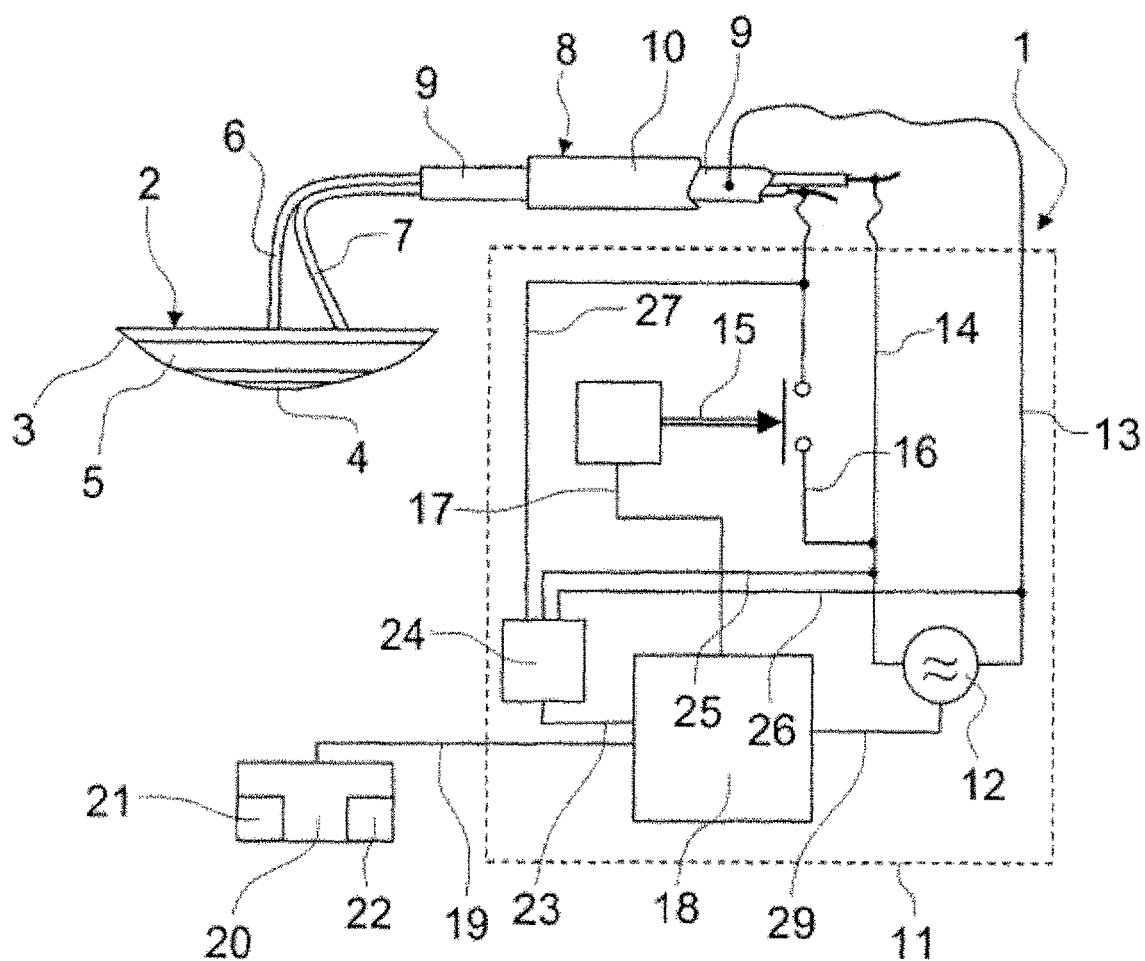
FIG. 1 shows a device according to the invention, having an electrode unit, which is shown in a side view with electric terminals, to a high-frequency generator, which is depicted as a block diagram.

The device 1 has an electrode unit 2, which forms a working area 3 having a convex protrusion in the diagram in FIG. 1.

Figure 2:
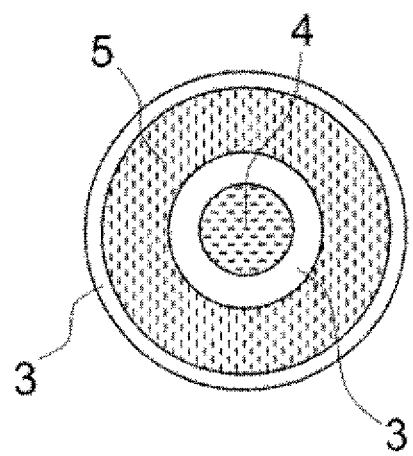
FIG. 2 shows a view from beneath of the electrode unit from FIG. 1.

FIG. 2 shows the working area 3 from beneath. It can be seen that two electrodes are arranged superficially on the working surface 3, consisting of a central first electrode 4 and a second electrode 5 arranged in a ring pattern around the former in the exemplary embodiment of FIGS. 1 and 2. The flat embodiment of the electrodes is understood here to mean that the electrodes extend over a surface component of the working area.

The two electrodes 4 and 5 are contacted to electric conductors, both of which are provided with external insulation, on the top side of the electrode unit 2 (not shown here). A first conductor 6 is connected to the first electrode 4 and a second conductor 7 is connected to the second electrode 5.

The two conductors 6, 7 run in an elongated electrode carrier 8. In the exemplary embodiment shown here, they are surrounded by a tubular neutral electrode 9, which is covered with insulation 10 over most of the length of the electrode carrier 8, in the distal end region, i.e., near the electrode unit 2, but exposed as a neutral electrode. When the electrode unit depicted here is situated in a conductive fluid, current can flow through the fluid between the electrodes 4 and 9 or 5 and 9.

The three electrodes 4, 5 and 9 are electrically connected to a high-frequency generator 11 as shown in FIG. 1. This has as the core component a high-frequency voltage source 12, which generates high-frequency voltage between two terminals. The one terminal is connected to the neutral electrode 9 by a line 13 and the other terminal is connected, by means of a line 14, to the first conductor 6 that supplies power to the first electrode 4. The connection to the conductors of the electrode carrier 8 is diagrammed in a highly schematic and provisional manner in FIG. 1. In a real application case, a three-pin plug connection would be provided here.

In the configuration explained so far, the device 1 shown in the figure would be fundamentally capable of operating. High-frequency current would flow through fluid or tissue, between the electrodes 4 and 9, would ignite and generate a plasma layer, namely only on the connected first electrode 4. The area of the latter is very small, so that rapid and reliable ignition then takes place.

Next a switch 15, which closes a line 16, thereby connecting the second line 7 to the line 14, may then be operated. The two electrodes 4 and 5 are now connected to the same terminal of the high-frequency voltage source 12. Plasma then burns on both electrodes 4 and 5, i.e., over a very large area, so that large areas of tissue can be processed very rapidly.

Figure 3:
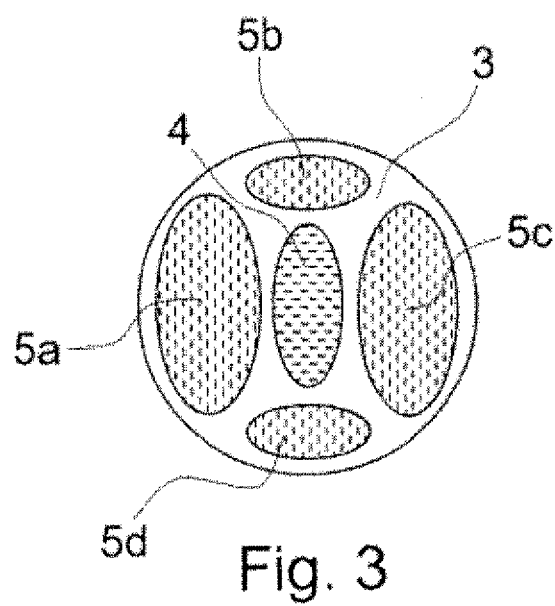
FIG. 3 shows a diagram according to FIG. 2 of an electrode unit in another embodiment.

FIG. 3 shows a variant of the working surface 3. The first electrode 4 here is designed like that in FIG. 2. However, the second electrode 5 is divided into four parts 5*a* through 5*d*, which are electrically interconnected and are connected to the second conductor 7. The effect of this design is similar to that of the one in FIG. 2.

The electrode division allocation in FIG. 3 also permits other applications. The central electrode 4 must not be used as the first electrode. For example, the area 5*b* may be used as the first electrode and all the other area parts are used as the second electrode. This may be advantageous when working with only the first electrode, for example, without switching on the second electrode. Thus, for example, it may be necessary to perform very fine work in small areas.

The switch 15 is controlled by a control unit 18 by means of a line 17. This control unit can analyze a number of parameters to control the switch 15 as a function thereof.

The control unit 18 is first connected by means of a line 19 to a foot operating part 20, which the operator can operate conveniently by foot. The foot operating part 20 has a main switch 21, which causes the control unit 18 to switch the high-frequency voltage source 12 on and off by means of a line 29. Using an auxiliary switch, the control unit 18 is made to control the switch 15 by means of the line 17 and to switch the second electrode 5 on or off.

The control unit receives measurement results over a line 23 from a measurement circuit 24, which determines the voltage between the lines 13 and 14, i.e., between the two terminals of the high-frequency voltage source 12 by means of lines 25 and 26. With a corresponding analysis, the measurement circuit may determine, for example, whether a plasma is burning. The control unit 18 can then control the switch 15 as a function thereof.

For correct control, it is also important to detect tissue contact. The measurement circuit 24 is also equipped for this. It is connected to the electrodes 4, 5 and 9 by corresponding lines and can determine the impedance between any two electrodes and can thus ascertain whether or not they are in contact with tissue.

The control unit 18 may be designed as a computer circuit, which takes into account the effects mentioned above in combination or in succession according to programs and weighs them against one another. It is not necessary to use all of the parameters mentioned above. The circuit of the HF generator 11 shown in FIG. 1 can be simplified.

The invention claimed is:

1. A high-frequency surgical device for treatment of a tissue surface, comprising:
   a high-frequency generator having a first terminal;
   an electrode unit including:
      a working surface for contacting the tissue surface,
      a first electrode which is formed on the working surface and connected to the first terminal of the high frequency generator, and
      a second electrode connectable to the first terminal of the high-frequency generator and formed on the working surface; and
   a measurement circuit configured to determine whether a plasma is burning; and
   a control unit configured to first connect the first electrode to the first terminal of the high-frequency generator, and to additionally connect the second electrode to the first terminal of the high-frequency generator after the measurement circuit detects that the plasma is burning.

2. The device according to claim 1, wherein:
   the measurement circuit is further configured to detect whether the first and second electrodes are in contact with the tissue surface, and
   the control unit is configured so that the additional connection of the high-frequency generator to the second electrode occurs after the measurement circuit detects that the first and second electrodes are in contact with the tissue surface.

3. The device according to claim 2, wherein the measurement circuit is configured to detect the tissue contact by determining the impedance between the first and second electrodes.

4. The device according to claim 1, wherein the control unit is further configured to connect the second electrode to the first terminal of the high-frequency generator, and/or to disconnect the second electrode to the first terminal of the high-frequency generator, in response to actuation of a user-operated switch.

5. The device according to claim 1, wherein the second electrode comprises separately arranged and jointly connectable electrode parts.

6. The device according to claim 1, wherein the control unit is configured to additionally connect the second electrode to the first terminal of the high-frequency generator as a function of the measurement circuit detecting that the plasma is burning.

7. An electrode unit of a high-frequency surgical device for treatment of a tissue surface having a high-frequency generator with a first terminal, comprising:
   a working surface for contacting the tissue surface,
   a first electrode which is formed on the working surface and connectable to the first terminal of the high-frequency generator, and
   a second electrode connectable to the first terminal of the high-frequency generator and formed on the working surface; and
   a control unit configured to first connect the first electrode to the first terminal of the high-frequency generator, and to additionally connect the second electrode to the first terminal of the high-frequency generator after a measurement circuit of the surgical device detects that the plasma is burning.

8. The electrode unit according to claim 7, wherein the control unit is configured to additionally connect the second electrode to the first terminal of the high-frequency generator as a function of the measurement circuit detecting that the plasma is burning.

9. A high-frequency generator of a high-frequency surgical device for treatment of a tissue surface having an electrode unit with a working surface for contacting the tissue surface, and first and second electrodes formed on the working surface, the high-frequency generator comprising:

a high-frequency voltage source generating a high-frequency voltage between first and second terminals thereof; and a control unit configured to first connect the first electrode to the first terminal, and to additionally connect the second electrode to the first terminal after a measurement circuit of the surgical device detects that the plasma is burning.

10. The high-frequency generator according to claim 9, wherein the control unit is configured to additionally connect the second electrode to the first terminal of the high-frequency generator as a function of the measurement circuit detecting that the plasma is burning.

* * * * *